10

(12) United States Patent
Melendez

(10) Patent No.: US 8,101,783 B1
(45) Date of Patent: Jan. 24, 2012

(54) TITANIUM-MALTOL COMPOUND AND METHOD OF SYNTHESIZING THE SAME

(75) Inventor: Enrique Melendez, Cabo Rojo, PR (US)

(73) Assignee: University of Puerto Rico, San Juan, PR (US)

( * ) Notice: Subject to any disclaimer, the term of this patent is extended or adjusted under 35 U.S.C. 154(b) by 513 days.

(21) Appl. No.: 12/271,273

(22) Filed: Nov. 14, 2008

Related U.S. Application Data

(60) Provisional application No. 60/987,915, filed on Nov. 14, 2007.

(51) Int. Cl.
*C07F 7/28* (2006.01)
*A61K 31/555* (2006.01)
(52) U.S. Cl. ........................................ 549/210; 514/184
(58) Field of Classification Search .................. 549/210; 514/184
See application file for complete search history.

(56) References Cited

OTHER PUBLICATIONS

Lamboy et al Inorganica Chimica Acta, vol. 360 (6), p. 2115-2120 (2007).*
Sobota et al, Chemistry a European Journal, vol. 7(5), p. 951-958 (2001).*

* cited by examiner

*Primary Examiner* — Bernard Dentz
(74) *Attorney, Agent, or Firm* — Hoglund & Pamias, PSC; Roberto J. Rios

(57) ABSTRACT

A novel compound showing anti-tumor properties was synthesized by reacting $Cp_2TiCl_2$ with maltol (3-hydroxy-2-methyl-4-pyrone) and a pH of 5.4, leading to a complete replacement of Cp and chloride ligands affording, $Ti(maltolato)_2(OH)_2$. The further crystallization of $Ti(maltolato)_2(OH)_2$ at pH of 8.4 leads to the formation of the novel anti-tumor compound $[Ti_4(maltolato)_8(\mu-O_4)]$.

19 Claims, 3 Drawing Sheets

IA

IB

IIA

IIB

TITANIUM-MALTOL COMPOUND AND METHOD OF SYNTHESIZING THE SAME

GOVERNMENT INTEREST

The claimed invention was made with U.S. Government support under grant number 2S06GM008103 awarded by the National Institutes of Health (NIH). The government has certain rights in this invention.

TECHNICAL FIELD

The present invention relates to a novel compound and a method of synthesizing the same. More specifically, the present invention relates a novel compound showing anti-tumor properties.

BACKGROUND OF THE INVENTION

Maltol (3-hydroxy-2-methyl-4-pyrone), is a naturally occurring, non-toxic compound and common food additive. Many biologically important metals form stable complexes with maltol. Its stability arises from the easiness to deprotonate and to behave as an anionic, bidentate metal chelator. There are numerous metal-maltol complexes used in bio-medical application. For instance, iron(III)-maltol complex has been used in the treatment of anemia and tris(maltolato) aluminum complex has found applications in the Alzheimer disease. Perhaps the most significant is bis(maltolato)oxovanadium(IV), which has been the subject of many chemical and physiological studies due to its potent insulinomimetic properties. This complex is an excellent glucose- and lipid-lowering insulin mimetics and it is currently evaluated in clinical trials.

Titanium(IV) complexes are widely used for a variety of purposes, mainly as catalysts in a diversity of organic reactions. But titanium(IV) complexes also have a role in the bioinorganic chemistry with two classical examples: titanocene dichloride ($Cp_2TiCl_2$) and budotitane ($Ti(bza)_2(OEt)_2$), which exhibit anti-cancer activities. With the discovery of the biological properties of these two Ti(IV) complexes, many research groups have devoted their efforts to synthesize new titanium complexes with enhanced antitumor activity.

Titanocene dichloride and budotitane possess the same limitation, low hydrolytic stability at physiological pH. As a result, the mechanistic aspects and hydrolysis products of these antitumor species remain mostly uncharacterized. The synthesis of hydrolytically stable Ti(IV) complexes at physiological pH (both organometallic and inorganic) with biological properties is still a challenge. Among oxygen containing chelating ligands, maltol has shown to form non-toxic complexes.

Thus, a new Ti(IV)-maltol complex with two reactive OH ligands has been synthesized at low pH. At high pH, this species further reacts to form a tetrameric species. These complexes could have potential for applications in catalysis and in the biomedical field.

SUMMARY OF THE INVENTION

Maltol has proven to be a versatile and non-toxic chelating ligand that has made a major contribution to the bioinorganic chemistry and catalysis. Therefore, the coordinating capabilities of maltol to Ti(IV) center are presented. First, maltol is able to replace organic ligands (in water) such as the well reputed Cp leading to the formation of a coordination compound. It is believed this is the first tetrameric titanium(IV) complex containing maltolate ligand. Similar tertameric complex has been reported with the guaiacol, a structural isomer of maltol but the bonding patterns between these two complexes are different. As investigated by spectroscopic methods, this complex can exist as a mixture of the monomeric/tetrameric species and their ratio is a function of the solution pH.

BRIEF DESCRIPTION OF THE DRAWINGS

These and other features, aspects, and advantages of the present invention will become better understood with reference to the following description, appended claims, and accompanying drawings where:

DETAILED DESCRIPTION OF THE INVENTION

The synthesis of Ti(IV)-maltol complex was accomplished by interaction of titanocene dichloride with two equivalents of maltol in aqueous solution at pH 5.4, leading to the formation of $Ti(maltolato)_2(OH)_2$ as a slightly water soluble yellow product. Alternatively, more than two (and preferably three) equivalents of maltol could be used to provide an excess and ensure completion of the reaction.

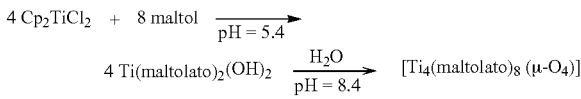

Not surprisingly, Ti(IV) being a hard acid and oxyphilic, readily reacts with maltol, an oxygen containing chelating ligand, to form dihydroxobis(maltolato)titanium(IV) complex. The initial product was characterized by spectroscopic and electrochemical methods. IR spectrum for $Ti(maltolato)_2(OH)_2$ shows four bands in the region of 1400-1620 $cm^{-1}$, which are typical of coordinated maltol ligand. The band at 1660 $cm^{-1}$ assigned to $\nu(C{=}O)$ in free maltol is shifted to 1620 $cm^{-1}$ while the combination bands of the $\nu(C{=}O)$ and $\nu(C{=}C)$ vibration modes at 1626 $cm^{-1}$ and 1565 $cm^{-1}$ are shifted to 1585 $cm^{-1}$ and 1518 $cm^{-1}$. A broad band at 3396 $cm^{-1}$ is observed and is attributed to the OH stretching.

To detect the exchangeable protons, $^1H$ NMR spectrum in DMSO-$d_6$ was recorded. Two broad signals corresponding to the OH protons are evident, in addition to two set of doublets for the H-5 and H-6 protons of each isomer in a ratio of 4:1 (cis:trans). Addition of $D_2O$ into the DMSO-$d_6$ solution produces the disappearance of these broad singlets, indicating that these signals belong to exchangeable OH protons.

To assign signals on the $^1H$ NMR spectral data, a few structural criteria was considered. For the cis isomers, the limited symmetry of the complex conferred by two chelating maltolate and two mutually cis-hydroxo ligands, makes the metal center chiral.

Figure 1:
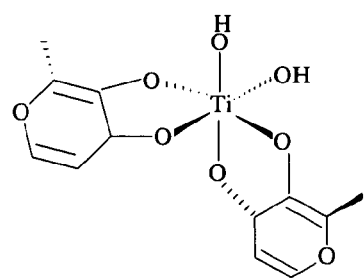
FIG. 1 shows several mixture compounds according to the present invention.
Figure 1:
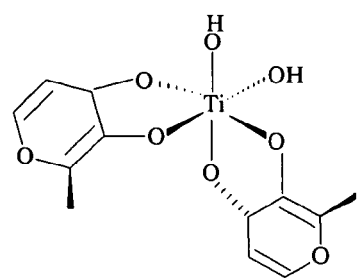
Figure 1:
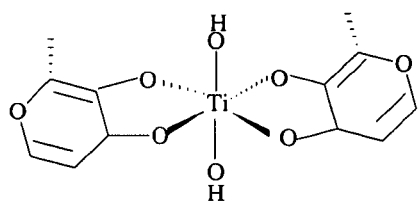
Figure 1:
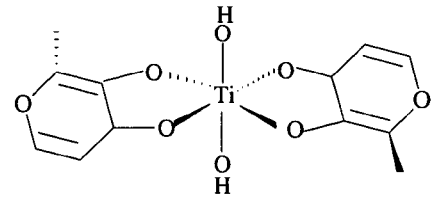

Given the fact that two set of resonances for the malotolato and hydroxo ligands at different ratios was observed, the presence of two different isomers with a $C_2$ axis or plane of symmetry was envisioned. There are two possibilities: a mixture of two cis-$Ti(maltolato)_2(OH)_2$ distereisomers IA and IB (containing the maltol methyl groups in the same and opposite directions, syn and anti to each other) or a mixture of cis IA and trans-dihydroxobis(maltolato)titanium(IV) complex IIA or IIB as shown in FIG. 1.

Extrapolating from the X-ray results (vide infra), IA should exist in solution. This isomer exhibits one set of maltol H-5 and H-6 signals as well as one OH signal. IA has a $C_2$ rotation axis. Therefore, in DMSO-$d_6$ solution, the $^1$H NMR spectrum should have four signals: two doublets for H-5, H-6 and two singlets for OH and $CH_3$ protons. On the other hand, isomer IB lacks of a $C_2$ rotation axis or plane of symmetry and two sets of H-5 and H-6 signals should be observed (the maltol ligands are not magnetically equivalent) as well as 2OH and $2CH_3$ signals. Since this is not the case, the second isomer should be IIA or IIB, trans-Ti(maltolato)$_2$(OH)$_2$, containing one set of H-5, H-6, OH and $CH_3$ signals.

The identity of these species in solution was investigated using ESI-MS spectroscopic techniques. In a mixture of $H_2O$/MeOH the predominant species in solution as [Ti(maltolato)$_2$(OH)$_2$—H]$^+$ with a parent peak at 329 m/z was identify. Further fragmentation of this parent peak, by ion trap methodology, demonstrated the loss of OH ligand. Elemental analysis corroborated this formula. This strongly suggests that the complex in solution at low pH is monomeric.

Figure 2:
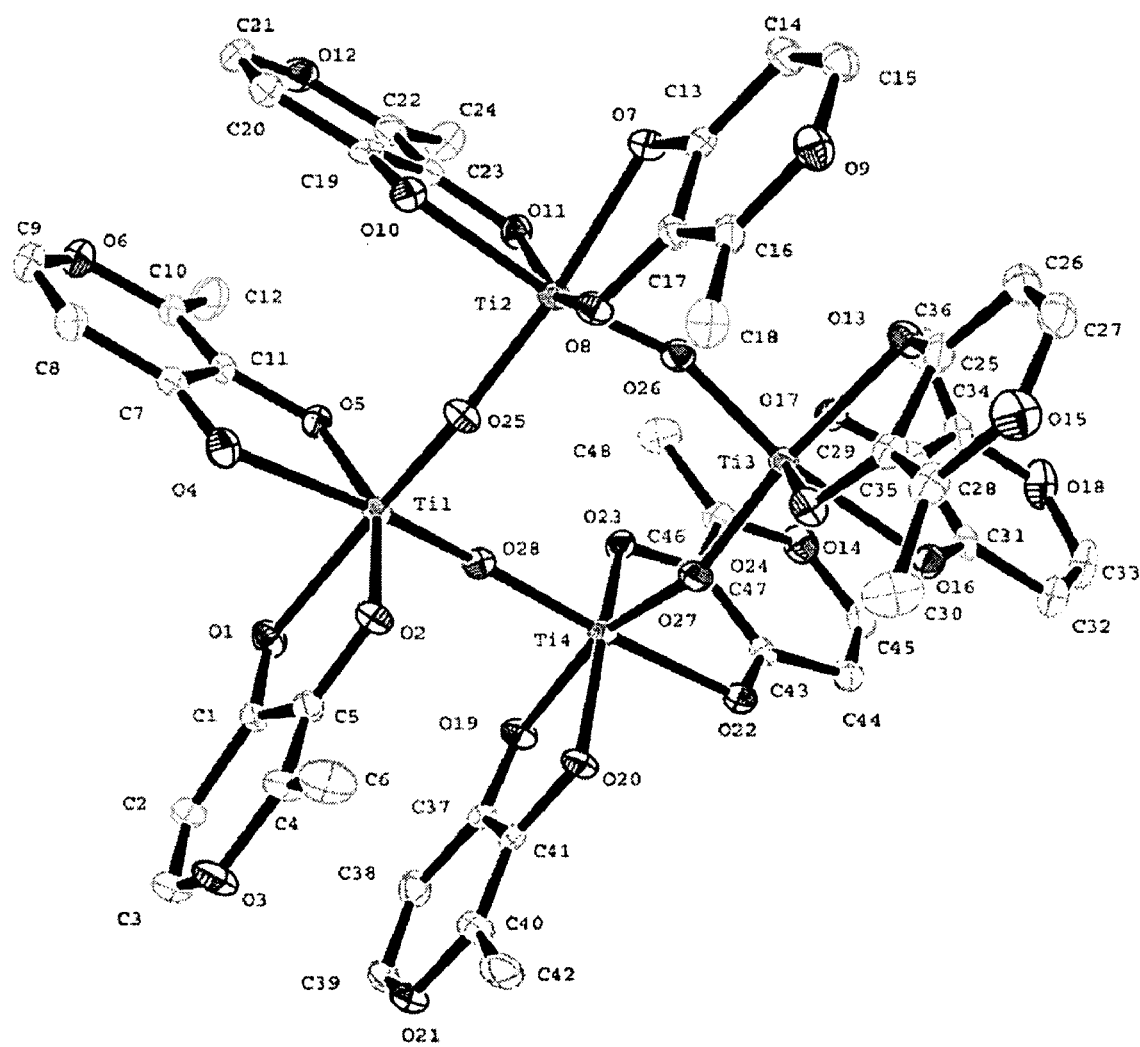
FIG. 2 shows single crystal X-ray solid state structure of the novel compound according to the invention.

Ti(maltolato)$_2$(OH)$_2$ is slightly soluble in water at low pH (5.4). However, at pH of 8.4 the complex becomes soluble in water but promotes tetramerization of the [Ti(maltolato)$_2$(OH)$_2$] species. In fact, this can be monitored by NMR spectroscopy. A pure sample of cis-[Ti(maltolato)$_2$(OH)$_2$] was dissolved in $D_2O$ at pH of 8.4. The $^1$H NMR spectrum of this solution showed two species in a ratio of 1:1. These two species belong most likely to cis-[Ti(maltolato)$_2$(OH)$_2$] and [Ti$_4$(maltolato)$_8$(μ-O)$_4$]. After 24 hours the tetrameric species continues increasing while the monomeric species decreases. Upon standing for two weeks, at pH of 8.4, this solution yields orange crystals suitable for X-ray diffraction. Evidently, Ti(maltolato)$_2$(OH)$_2$ further reacts to form a tetranuclear titanium complex, which crystallizes as a hydrate, [Ti$_4$(maltolato)$_8$(μ-O)$_4$].18H$_2$O, Single crystal X-ray structure determination was pursued on this high pH species, which solid state structure is illustrated in FIG. 2. The crystal data and structure refinement details as well as the bonding parameters are summarized below in Table 1 and Table 2, respectively.

TABLE 1

Crystal data and structure refinement for [Ti$_4$(2-maltol)$_8$(μ-O)$_4$]•18H$_2$O.

| | |
|---|---|
| Empirical formula | C$_{48}$H$_{76}$O$_{46}$Ti$_4$ |
| Formula weight | 1580.69 |
| Temperature | 100(2) K |
| Wavelength | 0.71073 Å |
| Crystal system | Monoclinic |
| Space group | P2(1)/c |
| Unit cell dimensions | a = 12.617(4) Å       α = 90°. |
| | b = 24.058(8) Å       β = 97.678(4)°. |
| | c = 22.686(7) Å       γ = 90°. |
| Volume | 6824(4) Å$^3$ |
| Z | 4 |
| Density (calculated) | 1.538 g/mL |
| Absorption coefficient | 0.559 mm$^{-1}$ |
| F(000) | 3280 |
| Crystal size | 0.30 × 0.30 × 0.20 mm$^3$ |
| θ range for data collection | 2.14 to 27.56°. |
| Index ranges | −15 <= h <= 15, −31 <= k <= 30, −29 <= l <= 28 |
| Reflections collected | 57671 |
| Independent reflections | 15416 [R(int) = 0.0702] |
| Completeness to theta = 25.00° | 99.9% |

TABLE 1-continued

Crystal data and structure refinement for [Ti$_4$(2-maltol)$_8$(μ-O)$_4$]•18H$_2$O.

| | |
|---|---|
| Absorption correction | Semi-empirical from equivalents |
| Max. and min transmission | 0.8964 and 0.8503 |
| Refinement method | Full-matrix least-squares on F$^2$ |
| Data/restraints/parameters | 15416/0/729 |
| Goodness-of-fit on F$^2$ | 0.914 |
| Final R indices [I > 2σ(I)] | R1 = 0.0459, wR2 = 0.1031 |
| R indices (all data) | R1 = 0.0708, wR2 = 0.1094 |
| Largest diff. peak and hole | 0.467 and −0.332 e.Å$^{-3}$ |

TABLE 2

Selected bond lengths [Å] and angles [°] for [Ti$_4$(η$^2$-maltol)$_8$(μ-O)$_4$]•18H$_2$O.

| | |
|---|---|
| C(1)-O(1) | 1.266(3) |
| C(1)-C(2) | 1.428(3) |
| C(1)-C(5) | 1.436(3) |
| C(2)-C(3) | 1.328(3) |
| C(3)-O(3) | 1.331(3) |
| C(4)-C(5) | 1.352(3) |
| C(4)-O(3) | 1.367(3) |
| C(4)-C(6) | 1.484(3) |
| C(5)-O(2) | 1.324(3) |
| O(1)-Ti(1) | 2.1797(17) |
| O(2)-Ti(1) | 1.9706(17) |
| O(4)-Ti(1) | 2.1495(17) |
| O(5)-Ti(1) | 1.9583(17) |
| O(25)-Ti(1) | 1.7990(16) |
| O(25)-Ti(2) | 1.8141(16) |
| O(28)-Ti(1) | 1.8050(16) |
| O(28)-Ti(4) | 1.8065(16) |
| Ti(1)-O(25)-Ti(2) | 148.37(10) |
| Ti(1)-O(28)-Ti(4) | 151.45(10) |
| O(25)-Ti(1)-O(28) | 100.18(7) |
| O(25)-Ti(1)-O(5) | 103.16(7) |
| O(28)-Ti(1)-O(5) | 91.73(7) |
| O(25)-Ti(1)-O(2) | 90.91(7) |
| O(28)-Ti(1)-O(2) | 104.30(7) |
| O(5)-Ti(1)-O(2) | 156.55(7) |
| O(25)-Ti(1)-O(4) | 91.30(7) |
| O(28)-Ti(1)-O(4) | 165.38(7) |
| O(5)-Ti(1)-O(4) | 76.75(7) |
| O(2)-Ti(1)-O(4) | 84.37(7) |
| O(25)-Ti(1)-O(1) | 166.92(7) |
| O(28)-Ti(1)-O(1) | 86.97(7) |
| O(5)-Ti(1)-O(1) | 87.43(6) |
| O(2)-Ti(1)-O(1) | 76.64(6) |
| O(4)-Ti(1)-O(1) | 83.60(7) |

As shown by X-ray diffraction study, the subject compound is tetrameric. Solid state structure of [Ti$_4$(maltolato)$_8$(μ-O)$_4$] consist of four Ti(IV) in a pseudo octahedral configuration linked by four oxo ligands. Similar structure but with guaiacolato ligand (a structural isomer of maltol) has been reported, [Ti$_4$(guaiacolato)$_8$(μ-O)$_4$]. The Ti$_4$O$_4$ moiety in [Ti$_4$(maltolato)$_8$(μ-O)$_4$] is non-planar, with alternate bridging oxygens above and below the Ti$_4$ plane. Since the four Ti coordination spheres and bonding parameters are similar, although not identical, only one unit, Ti(1) will discussed. As mentioned previously, Ti(1) consists of a pseudo-octahedral configuration with two bidentate maltolate and two mutually cis-μ-oxo ligands.

Two sets of Ti—O bonds can be identified in the titanium-maltol interaction. The Ti—O(deprotonated) bonds (Ti—O(5) and Ti—O(2)) are trans to each other, with bond distances (Ti—O(5) 1.9583(17) Å and Ti—O(2) 1.9706(17) Å) substantially shorter than the Ti—O(ketonic) bonds (Ti—O(1) 2.1797(17) Å and Ti—O(4) 2.1495(17) Å). This demonstrates the greater coordination and donating ability of the hydroxyl oxygens compared to ketonic oxygens. Ti—O(oxo) bonds are almost identical, 1.799(16) and 1.8050(16) Å.

The chelating angles (O(4)-Ti(1)-O(5), 76.75(7)° and O(1)-Ti(1)-O(2), 76.64(6)° are smaller than 90°, reflecting the strain created by the five member ring chelate while the cis-O(25)-Ti(1)-O(28) angle (100.18(7)° shows a deviation of 10° from the octahedral angles. In terms of the maltolato ligand, there is a small lengthening in the C=O(ketone) bonds (C(1)-O(10) 1.266(3) Å and C(7)-O(4) 1.276(3) Å) compared to free maltol, 1.248-1.254 Å. Within the maltol ring, carbon-carbon bond distances ranged from 1.328 to 1.436 Å. If a typical single carbon-carbon bond with length of 1.54 Å and a double bond with 1.32 Å are considered, it is evident that there is some degree of delocalization of the double bonds in the maltol ring.

Several differences can be observed when the subject structure is compared with the $[Ti_4(guaiacolato)_8(\mu-O)_4]$. First, the Ti—O(deprotonated) bonds of $[Ti_4(guaiacolato)_8(\mu O)_4]$ (1.901 Å) are shorter than Ti—O(deprotonated) bonds (1.9583(17) Å and 1.9706(17) Å) in $[Ti_4(maltolato)_8(\mu-O)_4]$, while the Ti—O(alkoxy) bonds in guaiacol complex (2.273 (11) Å and 2.289(12) Å) are longer than the Ti—O(ketonic) (2.1797(17) Å and 2.1495(17) Å) in the maltol complex, as a result of the different binding capabilities of these two oxygens. Second, the maltol ligands on adjacent titanium (i.e. Ti(1) and Ti(2) in $[Ti_4(maltolato)_8(\mu-O)_4]$) are arranged parallel to each other while the guaiacolate ligands are arranged perpendicular in $[Ti_4(guaiacolato)_8(\mu-O)_4]$. In the $Ti_4O_4$ moiety, $[Ti_4(maltolato)_8(\mu-O)_4]$ has two alternate bridging oxygens (O(25) and O(27)) above and the other two (O(26) and O(28)), below the $Ti_4$ plane, while for $[Ti_4(guaiacolato)_8(\mu-O)_4]$, two bridging oxygen are in the $Ti_4$ plane and the remaining two are one above and the other below the plane. On the other hand, similar expansion is observed in the cis-Ti—O (oxo) angles, 103° for $[Ti_4(guaiacolato)_8(\mu-O)_4]$ and 100° for $[Ti_4(maltolato)_8(\mu-O)_4]$.

Figure 3:
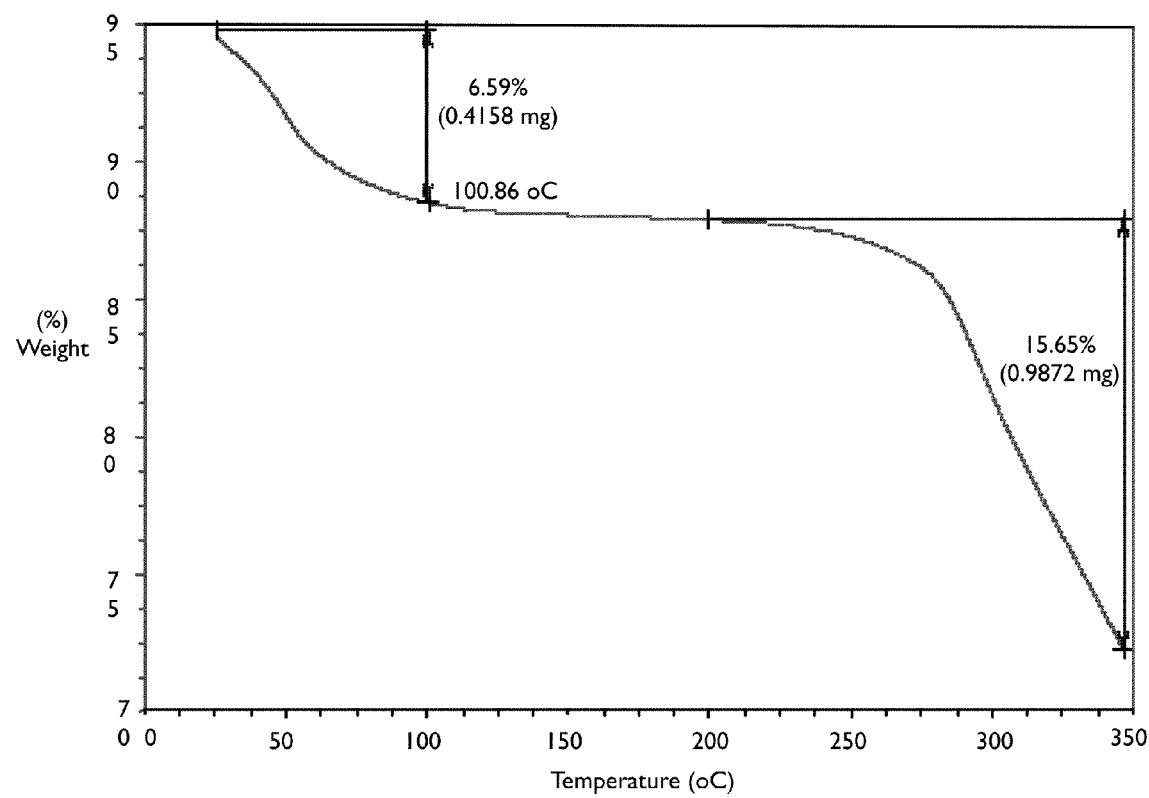
FIG. 3 shows a TGA plot according to an aspect of the invention.

Characterization of this tetrameric complex by NMR, IR and MS spectroscopic methods has been pursued. The $^1H$ NMR spectrum of the freshly dissolved $[Ti_4(maltol)_8(\mu-O)_4]$ crystals, in DMSO-$d_6$, shows one species, corresponding to the tetramer. In $D_2O$, the crystals also showed one species corresponding to $[Ti_4(maltolato)_8(\mu-O)_4]$ but after 3 hours, the presence of the cis-monomer is evident, reaching a ratio of the tetramer to cis-monomer of 7:1 (tetramer:monomer). This suggests that partial dissociation of the tetramer is taking place. The $[Ti_4(maltolato)_8(\mu-O)_4]\cdot18H_2O$ crystals are unstable and undergoes dehydration when removed from the mother liquor. Therefore, analytical data has been obtained consistent to $[Ti_4(maltolato)_8(O)_4]\cdot5.5H_2O$. This was further corroborated by TGA analysis which showed that this compound has five molecules of water as evidenced in FIG. 3. In addition, solution characterization by MS has been established. ESI-MS of this complex did not show a parent peak but showed fragments such as $[Ti (maltolato)_2 (OTi)_2]^+$, 423.1 m/z and $[Ti(maltolato)_2(OH)]^+$, 315.1 m/z. This data suggests that the complex in solution tends to be monomeric at low pH, and in the solid state the species isolated at high pH is tetrameric.

Electrochemical behavior of $Ti(maltolato)_2(OH)_2$ was investigated using cyclic voltammetry (cv). $Ti(maltolato)_2(OH)_2$ in $CH_2Cl_2/[NBu_4][BF_4]$ showed an irreversible cathodic wave at a potential of $(E_{red})$ −1.36 V, suggesting irreversible reduction of Ti(IV) to Ti(III), while no anodic wave was detected up to the solvent-electrolyte discharge potential. If this potential is compared with previously reported Ti(IV)-maltol and Ti(IV)-guaiacol complexes, it resembles to reduction potentials of monomeric species such as $Ti(maltolato)_2(OEt)_2$ (−1.0 V) and $Ti(maltolato)_2(Cl)_2$ (−1.55 V) and not to the tetrameric species $[Ti_4(guaiacolato)_8(\mu-O)_4]$ (−1.94 V). This evidence further suggests that the complex isolated at low pH is monomeric. Attempts to characterize the $[Ti_4(maltolato)_8(\mu-O)_4]$ by cyclic voltammetry failed due to the lack of solubility in $CH_2Cl_2$ and, in solvents such as DMSO or water no anodic/cathodic waves were detected up to the solvent-electrolyte discharge potential.

Methods and Materials

Titanocene dichloride was handled under dried nitrogen in Schlenk type anaerobic lines. The $Cp_2TiCl_2$ complex was obtained and used without further purification. Maltol was obtained and used as received. The purity of titanocene dichloride and maltol were checked by IR and/or by $^1H$ NMR spectroscopy. Water was doubly distilled, deionized and thoroughly saturated with dried nitrogen. All solvents for NMR measurements were 99.9% D purity grade. The dichloromethane ($CH_2Cl_2$) was distilled twice over $CaH_2$ and stored under nitrogen over molecular sieves.

Physical Measurements

FTIR spectra were recorded on a Bruker Vector-22 spectrophotometer with the samples as compressed KBr discs. The $^1H$ spectra were recorded on a 500 MHz Avance Bruker spectrometers under controlled temperature. Tetramethylsilane (TMS) and 3-(trimethylsilyl) propanesulfonic acid (DSS) were used as internal reference. Mass spectral data was obtained on a Bruker Daltonics Esquire 6000. The complexes were dissolved in a mixture of water/methanol (1:1) prior to mass spectral analysis. The electrospray positive ion was used as ionization mode during the MS experiment.

Electrochemical characterization was carried out on a BAS CV-50W voltammetric analyzer. Dichloromethane was used as a solvent for all electrochemical experiments. Once the solvent was dried over calcium hydride and distilled under nitrogen, it was stored in a round bottom flask over molecular sieves. Tetrabutylammonium tetrafluoroborate ($[NBu_4][BF_4]$) was used as supporting electrolyte in all electrochemical measurements. The supporting electrolyte was recrystallized from methanol and dried in vacuo prior to use.

A three-electrode configuration consisting of a glassy carbon working electrode, a platinum wire (Pt-wire) counter electrode, and a non-aqueous silver wire in contact with a solution of approximately (0.1M) $[NBu_4][BF_4]$ in dichloromethane ($CH_2Cl_2$) separated from the bulk solution by a fine glass frit as pseudo reference electrode. The internal reference is $[Fe(C_5H_5)_2]^{0/+}$ and potentials are quoted relative to SCE. The working electrode was polish with 0.05 μm alumina slurry for 1-2 min, and then rinsed with deionized water. This cleaning process was done before each cyclic voltammetry (CV) experiment. A sweep between 1.9 and −2.0 mV was performed.

The thermal analysis experiments were performed using a TAQ500 (TGA) instrument. The heating rate was 10° C./min for TGA analysis.

Synthesis of dihydroxobis(maltolato) titanium(IV), Ti(maltolato)$_2$(OH)$_2$ Complex In 80 ml of deionized water, under nitrogen, was charged with 200 mg (1.6 mmol) of maltol and, 200 mg (0.80 mmol) of titanocene dichloride. The pH was adjusted to 5.4 with 0.1M NaOH. After 96 hrs of stirring at room temperature, the reaction mixture was filtered and the yellow precipitate was dried under vacuum. Yield: 60% IR(KBr disc): 3396(br), 3074(w), 1620(m), 1586(s), 1518(m), 1476(s), 1276(s), 1246 (w), 1204(m), 928(w), 854(sh), 796(m), 728(m), 630(w), 543 (w), 475(w). $^1H$ NMR (DMSO-$d_6$, ambient, isomer I) δ: 8.273(bs, 1H), 6.529 (bs, 1H), 6.219(bs, 1H(OH)), 2.340 (bs, 3H). $^1H$ NMR (DMSO-$d_6$, ambient, isomer II) δ: 8.405 (d, 1H, J=5 Hz), 7.999 (bs, 1H(OH)), 6.728 (d, 1H, J=5 Hz), 2.395 (s, 3H). $^1$H NMR (D$_2$O, pH 8.4, ambient, isomer I, monomer) δ: 8.066 (d, 1H, J=5 Hz), 6.375 (d, 1H, J=5 Hz), 2.457(s, 3H). ESI-MS (positive mode), m/z (relative intensity): [Ti(η$^2$-maltolato)$_2$(OH)$_2$—H]$^+$ 327.2 (9.9), 328.2 (9.4), 329.1(100), 330.1(23), 331.1(10.1); [Ti(η$^2$-maltolato)$_2$(OH)]$^+$, m/z (relative intensity): 313.1(6.7), 314.1(10.8), 315.0 (100), 316.0 (18.1), 317 (26.7). Anal. Calc. for C$_{12}$H$_{12}$O$_8$Ti: C, 43.40; H, 3.64. Found: C, 43.25; H, 3.64.

[Ti$_4$(maltolato)$_8$(μ-O)$_4$] (tetramer) IR(KBr disc): 3418(br), 3074(w), 2920(vw), 1619(s), 1587(vs), 1516(m), 1472(s), 1392(w), 1368(w), 1276(s), 1243(m), 1203(s), 1092(w), 1040(w), 928(w), 854(sh), 796(s), 722(s), 628(w), 610(w), 543(m), 469(w). $^1$H NMR (DMSO-d$_6$, ambient) δ: 8.016 (d, 1H, J=5 Hz), 6.350(d, 1H, J=5 Hz), 2.389(s, 3H). $^1$H NMR (D$_2$O, pH 8.4, ambient) δ: 7.835 (d, 1H, J=5.5 Hz), 6.504 (d, 1H, J=5.5 Hz), 3.42(bs, H$_2$O), 2.314(s, 3H). ESI-MS (positive mode): m/z (relative intensity): [Ti(2-maltolato)$_2$(OTi)$_2$]$^+$, 422.2 (12.1), 423.1(100), 424.9 (31.1), 425.0 (13.6); [Ti(2-maltolato)$_2$(OH)]$^+$, 313.2 (5.8), 314.2 (7.3), 315.1 (100), 315.9 (46.3), 317.0 (8.5). Anal. Calc. for [Ti$_4$(2-maltolato)$_8$(O)$_4$].5.5H$_2$O: C, 42.53; H, 3.79. Found: C, 42.70; H, 3.70.

X-Ray Crystallographic Analysis

An orange plate cut to 0.30×0.20×0.20 mm in size was mounted on a cryoloop with Paratone® oil. Data was collected in a nitrogen gas stream at −173° C. Crystal-to-detector distance was 60 mm and exposure time was 10 seconds per frame using a scan width of 0.5°. Data collection was 99.9% complete to 25° in θ. A total of 57,671 reflections were collected covering the indices, h=−15 to 15, k=−31 to 30, l=−29 to 28. 15,416 reflections were found to be symmetry independent, with an R$_{int}$ of 0.0702 indicating that the data was of average quality (0.07). Indexing and unit cell refinement indicated a P centered, monoclinic lattice. The space group was found to be P 2$_1$/c (No. 14). The data was integrated using the Bruker SAINT Software program and scaled using the Bruker SADABS software program. Solution by direct methods (SIR-2004) produced a complete heavy atom phasing model consistent with the proposed structure. All non-hydrogen atoms were refined anisotropically by full-matrix least-squares (SHELXL-97). All hydrogen atoms were placed using a riding model and their positions constrained relative to their parent atom using the appropriate HFIX command in SHELXL-97. 18 H$_2$O molecules co-crystallized with the target complex. The water molecules were treated by removal of their electron contributions using the Squeeze routine in the PLATON software package.

While the preferred embodiments of the present invention have been illustrated and described, it will be clear that the present invention is not limited to these embodiments only. Numerous modifications, changes, variations, substitutions and equivalents will be apparent to those skilled in the art without departing from the spirit and scope of the present invention as described in the claims.

I claim:

1. A method of preparing a compound suitable for use as an anti-tumor agent comprising:
   reacting Cp$_2$TiCl$_2$ with maltol in distilled water.

2. The method of claim 1, further comprising:
   adjusting the pH to about 5.4.

3. The method of claim 2, further comprising:
   stirring the resulting solution for a first predetermined amount of time at a first predetermined temperature.

4. The method of claim 3, wherein a resulting solid is isolated and dried for a second predetermined amount of time.

5. The method of claim 4, further comprising:
   dissolving said dried resulting solid in distilled water and adjusting the pH to about 8.4.

6. The method of claim 5, further comprising:
   stirring the solution for a third predetermined amount of time and allowing said solution to solidify for a fourth predetermined amount of time.

7. The method of claim 1, wherein said Cp$_2$TiCl$_2$ is reacted with three equivalents of maltol.

8. The method of claim 2, wherein said pH is adjusted to about 5.4 with about 0.1M of NaOH.

9. The method of claim 3, wherein said first predetermined amount of time is about 96 hours and said first predetermined temperature is about room temperature.

10. The method of claim 4, wherein said second predetermined amount of time is about 6 hours.

11. The method of claim 5, wherein said pH is adjusted to about 8.4 with about 0.1M of NaOH.

12. The method of claim 6, wherein said third predetermined amount of time is about one hour and said fourth predetermined amount of time is about one week.

13. The method of claim 4, wherein said resulting solid is isolated by filtration.

14. The method of claim 13, wherein said resulting solid is washed with distilled water after said filtration.

15. The method of claim 4, wherein said resulting solid is dried in vacuo.

16. The method of claim 1, wherein said compound shows antitumor activity against colon cancer.

17. A method of preparing a compound suitable for use as an anti-tumor agent comprising:
   synthesizing Ti$_4$(maltolato)$_8$(μ-O)$_4$ from Ti(maltolato)$_2$(OH)$_2$.

18. An anti-tumor drug comprising the compound prepared by the method of claim 17.

19. A compound suitable for use as an anti-tumor agent comprising:
   Ti$_4$(maltolato)$_8$(μ-O)$_4$.

* * * * *